United States Patent [19]
Clapham

[11] Patent Number: 6,068,625
[45] Date of Patent: May 30, 2000

[54] METHOD AND SYSTEM FOR REMOVING AN EPITHELIAL LAYER FROM A CORNEA

[75] Inventor: Terrance N. Clapham, Saratoga, Calif.

[73] Assignee: VISX Incorporated, Santa Clara, Calif.

[21] Appl. No.: 09/022,774

[22] Filed: Feb. 12, 1998

[51] Int. Cl.⁷ ............................................. A61B 18/18
[52] U.S. Cl. .................................................. 606/4; 606/2
[58] Field of Search ........................... 606/4, 5, 6, 10, 606/11, 12

[56] References Cited

U.S. PATENT DOCUMENTS

| | | | |
|---|---|---|---|
| 4,178,418 | 12/1979 | Croset et al. | 429/27 |
| 4,665,913 | 5/1987 | L'Esperance, Jr. | 606/5 |
| 4,669,466 | 6/1987 | L'Esperance | 606/5 |
| 4,718,418 | 1/1988 | L'Esperance, Jr. | 606/5 |
| 4,732,148 | 3/1988 | L'Esperance, Jr. | 606/5 |
| 4,770,172 | 9/1988 | L'Esperance, Jr. | 606/5 |
| 4,773,414 | 9/1988 | L'Esperance, Jr. | 606/5 |
| 4,941,093 | 7/1990 | Marshall et al. | 361/413.01 |
| 4,994,058 | 2/1991 | Raven et al. | 606/5 |
| 5,108,388 | 4/1992 | Trokel | 606/5 |
| 5,123,902 | 6/1992 | Müller et al. | 604/21 |
| 5,163,934 | 11/1992 | Munnerlyn | 606/5 |
| 5,207,668 | 5/1993 | L'Esperance, Jr. | 606/5 |
| 5,219,343 | 6/1993 | L'Esperance, Jr. | 606/5 |
| 5,279,298 | 1/1994 | Flower | 606/4 |
| 5,279,611 | 1/1994 | McDonnell et al. | 606/4 |
| 5,391,165 | 2/1995 | Fountain et al. | 606/4 |
| 5,423,801 | 6/1995 | Marshall et al. | 606/5 |
| 5,505,724 | 4/1996 | Steinert | 606/5 |
| 5,549,599 | 8/1996 | Sumiya | 606/10 |
| 5,630,810 | 5/1997 | Machat | 606/5 |
| 5,634,920 | 6/1997 | Hohla | 606/12 |
| 5,646,791 | 7/1997 | Glockler | 359/831 |
| 5,683,379 | 11/1997 | Hohla | 606/5 |
| 5,827,264 | 10/1998 | Hohla | 606/5 |

*Primary Examiner*—Linda C. M. Dvorak
*Assistant Examiner*—Soja Harris
*Attorney, Agent, or Firm*—Townsend and Townsend and Crew LLP

[57] ABSTRACT

Laser ablative radiation is used to remove the epithelial layer from over the stromal layer in a cornea. While uniform exposure of a single or scanned ablative beam will generally remove peripheral portions of the epithelial layer faster than central portions, such non-uniform removal is corrected by patterning the beam to reduce peripheral exposure relative to central exposure.

8 Claims, 7 Drawing Sheets

METHOD AND SYSTEM FOR REMOVING AN EPITHELIAL LAYER FROM A CORNEA

BACKGROUND OF THE INVENTION

1. Field of the Invention

The present invention is directed to methods, systems, and computer programs for removing an epithelial layer from a cornea of an eye. In particular, the present invention is directed at methods, systems, and computer programs for controlling exposure of the epithelial layer to ablative radiation in order to effect uniform and complete removal of the epithelial layer over a treatment region.

Ultraviolet and infrared laser based systems and methods are known for enabling ophthalmological surgery on the exposed surface of the cornea in order to correct vision defects. These procedures, generally referred to as photorefractive keratectomy, generally employ an ultraviolet or infrared laser to remove a microscopic layer of anterior stromal tissue from the cornea to alter its refractive power. In ultraviolet laser ablation procedures, the radiation ablates corneal tissue in a photodecomposition that does not cause thermal damage to adjacent and underlying tissue. Molecules at the irradiated surface are broken into smaller volatile fragments without heating the remaining substrate; the mechanism of the ablation is photochemical, i.e. the direct breaking of intermolecular bonds. The ablation removes stromal tissue to change the contour of the cornea for various purposes, such as correcting myopia, hyperopia, and astigmatism. Such systems and methods are disclosed in the following U.S. patents and patent applications, the disclosures of which are hereby incorporated by reference: U.S. Pat. No. 4,665,913 issued May 19, 1987 for "METHOD FOR OPHTHALMOLOGICAL SURGERY"; U.S. Pat. No. 4,669,466 issued Jun. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. patent application Ser. No. 109,812 filed Oct. 16, 1987 for "LASER SURGERY METHOD AND APPARATUS"; U.S. Patent No. 5,163,934 issued Nov. 17, 1992 for "PHOTOREFRACTIVE KERATECTOMY"; U.S. patent application Ser. No. 08/368,799, filed Jan. 4, 1995 for "METHOD AND APPARATUS FOR TEMPORAL AND SPATIAL BEAM INTEGRATION"; U.S. patent application Ser. No. 08/138,552, filed Oct. 15, 1993 for "METHOD AND APPARATUS FOR COMBINED CYLINDRICAL AND SPHERICAL EYE CORRECTIONS"; and U.S. patent application Ser. No. 08/058,599, filed May 7, 1993 for "METHOD AND SYSTEM FOR LASER TREATMENT OF REFRACTIVE ERRORS USING OFFSET IMAGING".

Of particular interest to the present invention, before the stromal tissue can be treated, an overlying layer of epithelial cells, referred to as the epithelial layer, is often removed. The epithelial layer is typically about 50 µm thick, and removal has commonly been performed using a blunt spatula or other instrument for scraping the layer from the stroma.

Scraping the epithelial layer is disadvantageous in a number of respects. Use of a scraping instrument can impart irregularities to the stromal layer which can adversely affect subsequent treatment of the stroma using the laser radiation. Similarly, incomplete removal of the epithelial layer may also adversely affect subsequent reshaping of the stroma. Moreover, since the scraping is performed manually, it is usually necessary to remove more of the epithelium from an area larger than will actually be treated by the laser. The removal of extra epithelial tissue can increase the time necessary for healing. Additionally, use of a scraping instrument presents a small, but finite risk of infection to the patient.

For all of these reasons, the use of laser energy to remove the epithelial layer has been proposed. The use of laser energy avoids at least most of the complications associated with use of a scraping instrument, as described above. Moreover, use of the same laser which is used for subsequent treatment of the stroma would be particularly convenient and lead to a reduction in the overall time required for the treatment protocol.

Prior attempts to utilize single beam ablative radiation for removal of the epithelial layer of a cornea, however, have been limited by excessive removal of peripheral portions of the treated region, typically resulting in unintended removal of stromal tissue. Referring to FIGS. 1–3, laser systems 10 have been focused through apertures 12 so that a single beam of ablative radiation 14 is directed at the epithelial layer E disposed over a stromal layer S in a cornea C. It has been found that exposure of the epithelial layer E for a time sufficient to remove the full thickness of the layer at the center line CL of treatment (FIG. 2) results in excess removal of corneal material in the peripheral region P, as illustrated in FIG. 2. As can be seen, the epithelial layer E has been completely removed in a peripheral region P. In addition, a portion of the stromal layer S in peripheral region P has also been removed. Such reshaping of the exposed stromal surface prior to corrective treatment can adversely affect the subsequent treatment. While the initial, unintended reshaping of the stromal surface can be offset, for example, in the case of hyperopia, by increasing the diopter (flattening) of the subsequent laser treatment, the combined initial removal of the stromal material and subsequent correction of the initial removal results in a depression or well W being formed in the stromal layer, as illustrated in FIG. 3. While such an outcome has not been found to be clinically significant, it is undesirable to remove more stromal material than the amount which is necessary to effect the desired corneal reshaping.

For these reasons, it would be desirable to provide improved methods and systems for using ablative radiation to remove the epithelial layer from a cornea prior to photorefractive keratectomy to treat the underlying stromal layer. In particular, it would be desirable to provide methods and systems which remove the epithelial layer completely but without any significant removal of the underlying stromal layer. Such methods and systems should preferably utilize the same laser source and control systems employed in the subsequent photorefractive keratectomy treatment, should be simple to perform, and should overcome at least some of the deficiencies noted above.

2. Description of the Background Art

U.S. Pat. No. 5,505,724 describes use of a laser system for removing an epithelial layer prior to photorefractive keratectomy. While the '724 patent suggests that ablation of the epithelium in different areas of the treatment region should be the same, there is little description of how to achieve such a result.

U.S. Pat. No. 5,549,599 describes the use of a laser for removing epithelial and stromal tissue from an eye in successive steps. Switching from an epithelial removal mode to a stromal removal mode is performed manually or automatically based on a change in observed fluorescence. U.S. Pat. No. 5,634,920 describes the use of a laser for removing epithelial and stromal tissue from an eye. Epithelial removal is performed using a large beam until a change in fluorescence is observed. Different diameter beams are then defected at different remaining portions of the epithelium until it is entirely removed.

SUMMARY OF THE INVENTION

The present invention provides methods, systems, and computer programs for removing an epithelial layer from over stroma in a cornea of a patient, particularly for patients about to undergo photorefractive keratectomy. The methods comprise irradiating a region of the epithelial layer with a beam of ablative radiation to remove the epithelial layer down to Bowman's layer over the stroma. In order to assure uniform removal of the epithelial layer over the entire irradiated region, the ablative radiation is patterned to reduce actual exposure of an outer peripheral portion during at least part of the total exposure. The reduction of peripheral exposure is selected to offset excess ablation of the cornea (particularly within the stromal layer) over the peripheral portion which would occur in the absence of such patterning.

In a first embodiment, the ablative radiation will comprise a single beam, typically having a circular cross-section with a diameter in the range from about 0.6 mm to 7.0 mm, preferably from 0.6 mm to 6.5 mm, with a substantially uniform intensity across its width. The beam intensity is typically in the range from 110 to 220 mJ/cm$^2$, and the beam will usually be pulsed in a manner similar to that employed in photorefractive keratectomy of the stroma. Use of such single beams allows tissue removal over the entire radiated region without moving the laser relative to the eye.

When using the single beam, the patterning step typically comprises disposing a diametrically adjustable aperture between a laser radiation source and the cornea. For example, the aperture may be an iris in a conventional photorefractive keratectomy laser system. The diameter of the aperture is then adjusted so that the aperture is open to expose substantially the entire region of the epithelial layer to be treated during a portion of the total exposure period. During another portion of the total exposure period, however, the diameter of the aperture is adjusted between its open position and a closed position so that the exposure of the peripherally outer portions of the treatment region is progressively reduced relative to the central and inner portions. Typically, the diameter of the aperture will be adjusted (closed or opened) at a uniform rate over that portion of the total treatment.

The present invention may also find applications within scanning beam systems. Hence, in a second embodiment, the ablative radiation will be produced by a scanning beam, typically having a circular cross-section with a diameter in the range from about 0.6 mm to 2.0 mm. Such scanning beam laser ablation systems are described in U.S. Pat. Nos. 4,178,418, 4,665,913, 5,391,165, and 5,683,379, the full disclosures of which are incorporated herein by reference. In the case of such scanning beam systems, the total radiation exposure to different portions of the treated region of the epithelial layer may be adjusted by controlling the total amount of time the scanned beam is directed against each portion, or by controlling the number of laser pulses directed against each portion. Varying the number of pulses, for example, by cycling the laser pulses and scanning system to ablate alternating portions of the eye, may limit heat buildup, and can also provide a gradual correction which will at least partially correct vision if the procedure is interrupted or prematurely halted. The laser and/or laser delivery system will typically be controlled so that the peripheral portion of the total treated region of the cornea, or the peripheral portion of the cornea treated by each laser pulse, receives a lesser total radiation exposure than the corresponding more central portions. In this way, excess removal of corneal material, and in particular the unintended removal of the stromal material, can be corrected.

Alternatively, the single or scanned beam ablative radiation can be patterned using an ablation mask which is configured to reduce exposure of the peripheral portions of the removal region relative to the central portions and center line.

Systems according to the present invention comprise a laser which produces a single, or possibly a scanned, beam of ablative radiation and a patterning means to reduce exposure of an outer peripheral portion of a corneal treatment region relative to a central portion thereof. In the case of the single beam, the patterning means will effect such exposure reduction during a part of a total exposure period in order to offset excess ablation of a cornea which would occur in the absence of the patterning. A first exemplary patterning means comprises a diametrically adjustable aperture and a controller for adjusting the diameter of the aperture. A tangible medium comprising computer-readable code is further provided to impart instructions to the controller to adjust the diameter of the aperture over a total exposure period, generally according to the methods set forth above.

If the invention is used in a scanned beam system, the patterning means may comprise a controller capable of adjusting the number of laser pulses or the scan or dwell time of the scanned beam so that peripheral portions of the treatment region receive a lesser total exposure of ablative radiation than do the more central regions.

An additional exemplary patterning means useful with both the single and scanned beam system comprises an ablation mask configured to reduce exposure of the peripheral portion of the cornea relative to a central portion of a treatment region thereon.

In yet another aspect, the present invention comprises a computer program comprising a tangible medium and computer-readable code setting forth any of the methods described above.

DESCRIPTION OF THE SPECIFIC EMBODIMENTS

The present invention includes methods, systems, and computer programs for applying laser ablative radiation to remove an epithelial layer from a cornea of an eye. Removal of the epithelial layer will usually be performed immediately prior to performing selective ablation of the underlying stromal layer of the cornea in connection with a photorefractive keratectomy procedure. The systems of the present invention will utilize a single or scanned beam of ablative radiation generated by a laser in a conventional manner, and may conveniently comprise presently available commercially systems intended for photorefractive keratectomy which have been programmed or otherwise modified to perform the epithelial layer removal methods as described in detail below. In particular, the systems of the present invention may be based on the STAR™ Excimer Laser System which is commercially available from VISX, Incorporated of Santa Clara, Calif., assignee of the present application. In particular, the STAR™ Excimer Laser System may be programmed to perform the methods of the present invention by providing a computer program in the form of a tangible medium comprising computer-readable code setting forth the methods described in more detail below.

Figure 4:
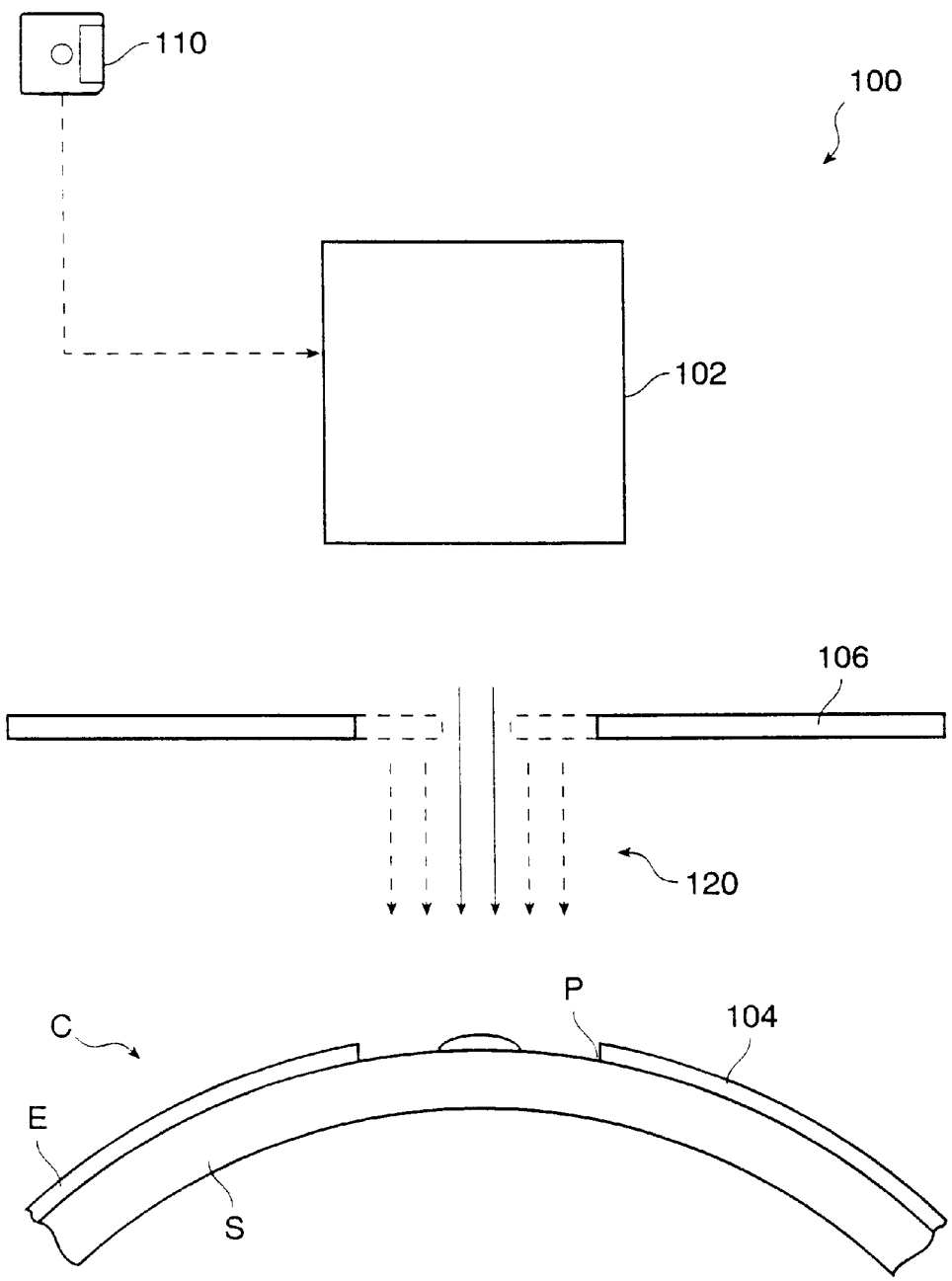
FIG. 4 illustrates a system constructed in accordance with the principles of the present invention.

Referring now to FIG. 4, a system 100 useful for performing the methods of the present invention will comprise a laser system 102 which preferably includes an argon-fluorine laser with a 193 nanometer wavelength output designed to provide feedback-stabilized fluency of 160 millijoules per cm$^2$ at the cornea of patient's eye 104 when delivered through associated optics and equipment, generally as arranged in the STAR™ Excimer Laser System. The system 100 further includes a diametrically adjustable aperture 106, typically a controllable iris, which is disposed between the laser source in system 102 and the eye 104. The laser 102 produces a single beam of ablative radiation, and the diameter of the beam which reaches the eye 104 is adjusted by controlling the diameter of aperture 106. Other ancillary components of the laser surgery system 20 which are not necessary to an understanding of the invention, such as a high resolution microscope, a video monitor for the microscope, a patient eye retention system, and an ablation effluent evacuator/filter, as well as the gas delivery system, have been omitted from the drawings for simplicity. Similarly, the keyboard, display, and conventional PC subsystem components (e.g., flexible and hard disk drives, memory boards and the like) have been omitted from an associated PC work station. Further details of suitable system for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are hereby incorporated herein by reference.

The laser subsystem 102 is programmable through the associated PC workstation using any conventional programming technique. Conveniently, a computer program 110 in the form of a computer-readable disk or other conventional medium is provided as part of the system 100. The computer program 110 encodes the methods for removing an epithelial layer according to the present invention, as described in more detail below.

Figure 1:
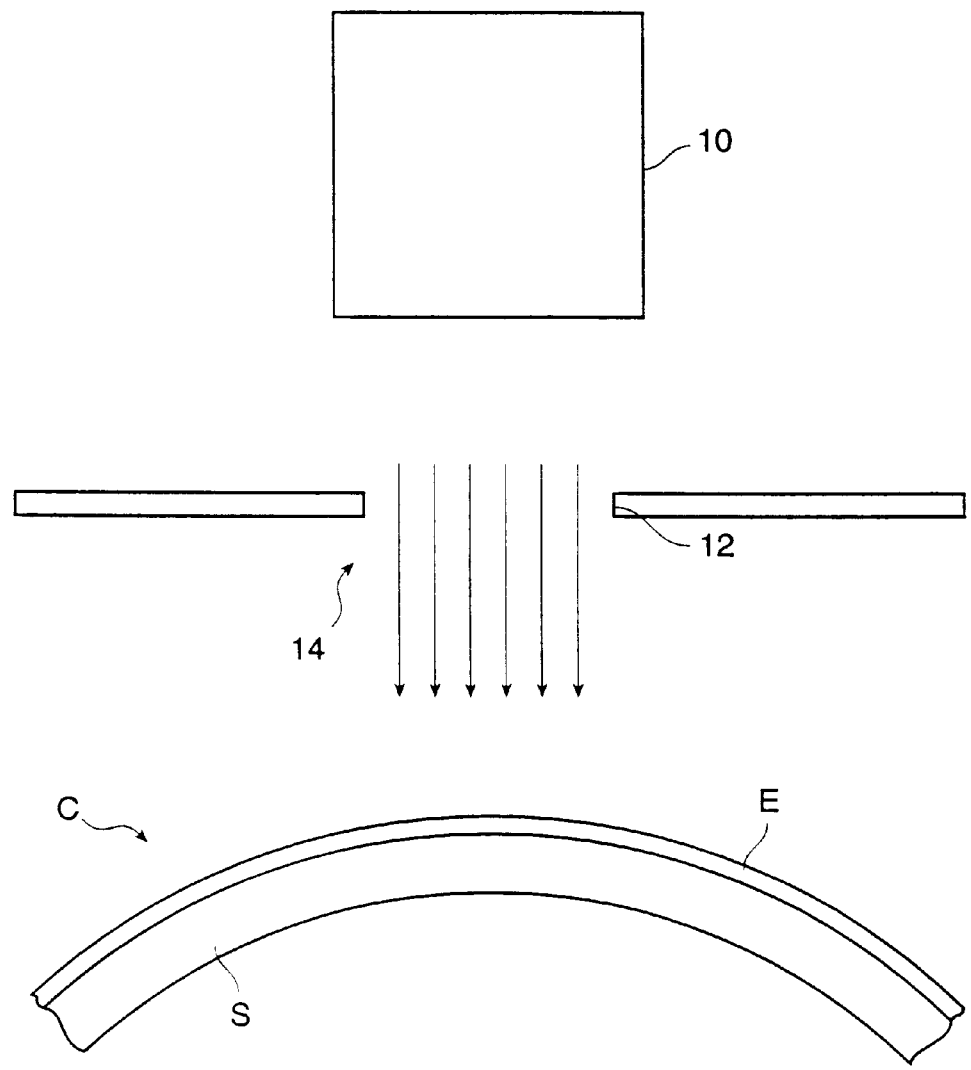
FIGS. 1–3 illustrate the prior art systems and methods discussed above in the Background of the Invention.
Figure 2:
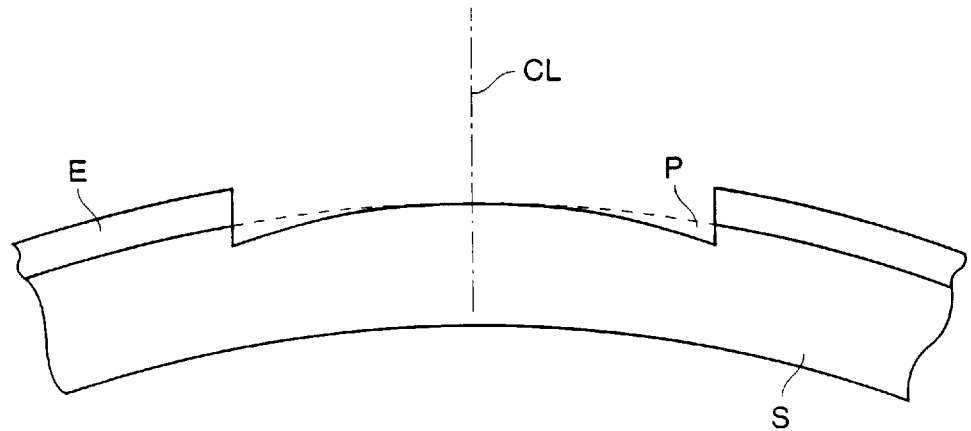
Figure 3:
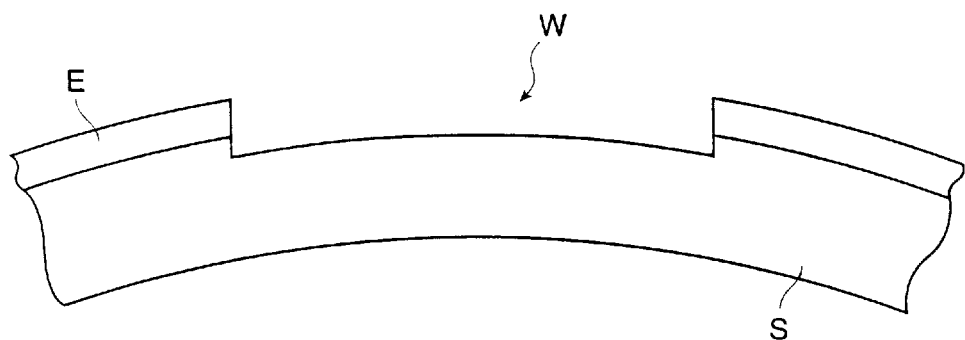

The eye 104 comprises the cornea C, the epithelial layer E, and the underlying stromal layer S. Ablative radiation 120 from the laser subsystem 102 is directed against the epithelial layer E of the cornea C through the diametrically adjustable aperture 106. For reasons which are not fully understood, when the ablative radiation is directed against the epithelial layer, the rate of ablation near the periphery P of the exposed region is greater than that near the center of the region. Thus, if no patterning or other adjustments of the radiation are performed, the profile of the cornea will appear as shown in prior art FIG. 2 described above. In order to offset such uneven removal rates of the cornea, the present invention relies on patterning the ablative radiation so that the peripheral portions of the region being treated are exposed to less total energy than are the central portions, as can be done in a variety of ways.

Figure 5:
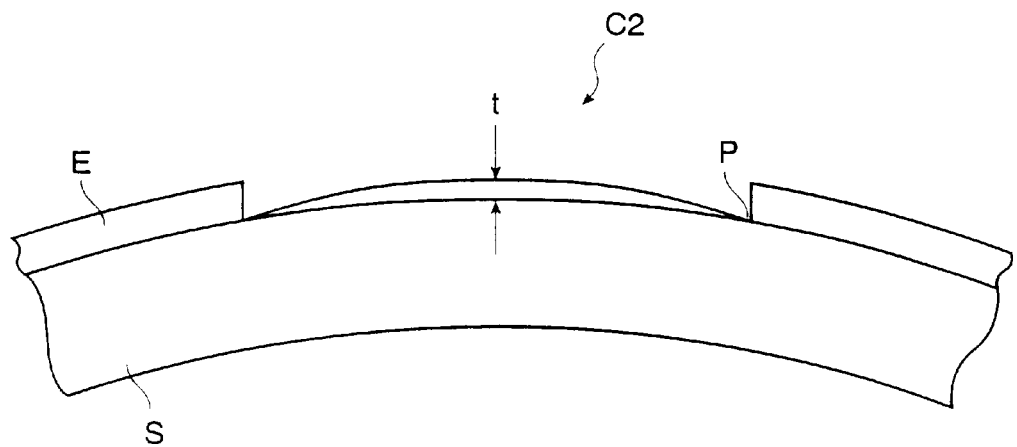
FIG. 5 illustrates the cross-section of a cornea being treated by a first exemplary method utilizing the system of FIG. 4.

For example, referring to FIG. 5, ablation can initially be performed with the aperture 106 fully open, i.e. open to a diameter equal to the desired diameter of epithelial removal, usually in the range from 2.0 mm to 7.0 mm. The full beam of ablative radiation can be applied to the epithelial layer E for a time period sufficient to remove the periphery P down to the anterior surface of the stromal layer S.

As can be seen in FIG. 5, even though the peripheral regions reached the stromal layer S, the central region will have a depth of epithelial tissue remaining, typically with a thickness in the range from 1.0 $\mu$m to 10.0 $\mu$m. In order to remove the remaining epithelial material, the aperture 106 can be adjusted to differentially apply increasingly greater amounts of the ablative radiation along concentric lines moving progressively toward the center line of the treatment region. This can be done either by starting with the aperture 106 fully opened and closing the aperture to a substantially closed configuration over time or vice versa. In either case, the rate of opening or closing is selected provide the proper amount of energy to remove the dome-shaped epithelial layer remaining, as illustrated in FIG. 5. Conveniently, it has been found that the epithelial material remaining may be removed by adjusting the aperture 106 in a manner similar to that used for flattening the stromal layer by from 1 diopter to 2 diopters, typically about 1.5 diopter.

Figure 6:
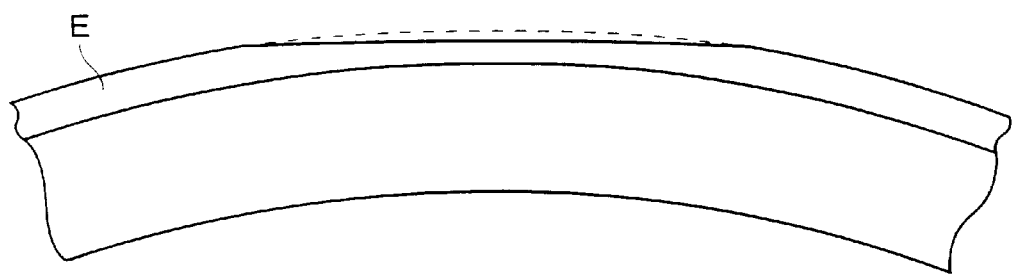
FIG. 6 illustrates the cross-section of a cornea being treated with a second exemplary method utilizing the system of FIG. 4.
Figure 7:
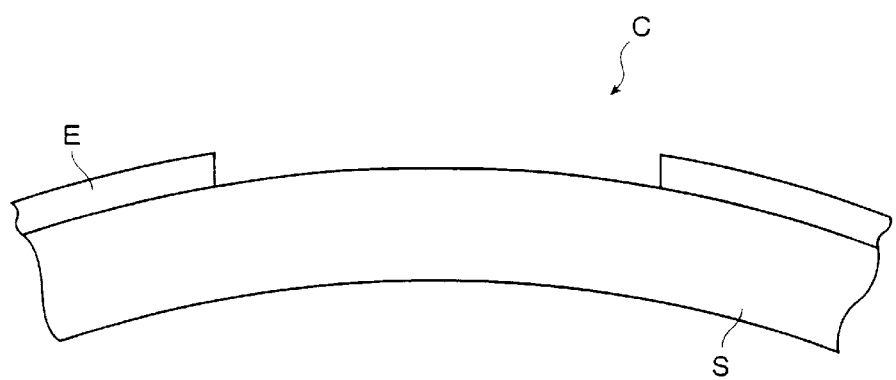
FIG. 7 illustrates the cornea of either FIG. 5 or FIG. 6 after treatment according to a method of the present invention.

Alternatively, the epithelial layer E can be "flattened" prior to removal of the peripheral material, as illustrated in FIG. 6. The aperture 106 is adjusted to open or close in order to flatten the upper surface of the epithelial layer, again typically by 1 to 2 diopters. After the upper surface has been flattened, the ablative radiation is exposed through the fully open aperture 106 until the epithelial material is fully removed. Thus, the methods described in connection with both FIGS. 5 and 6 result in the complete removal of the epithelial layer E without significant removal of the stromal material, generally as illustrated in FIG. 7.

Figure 4A:
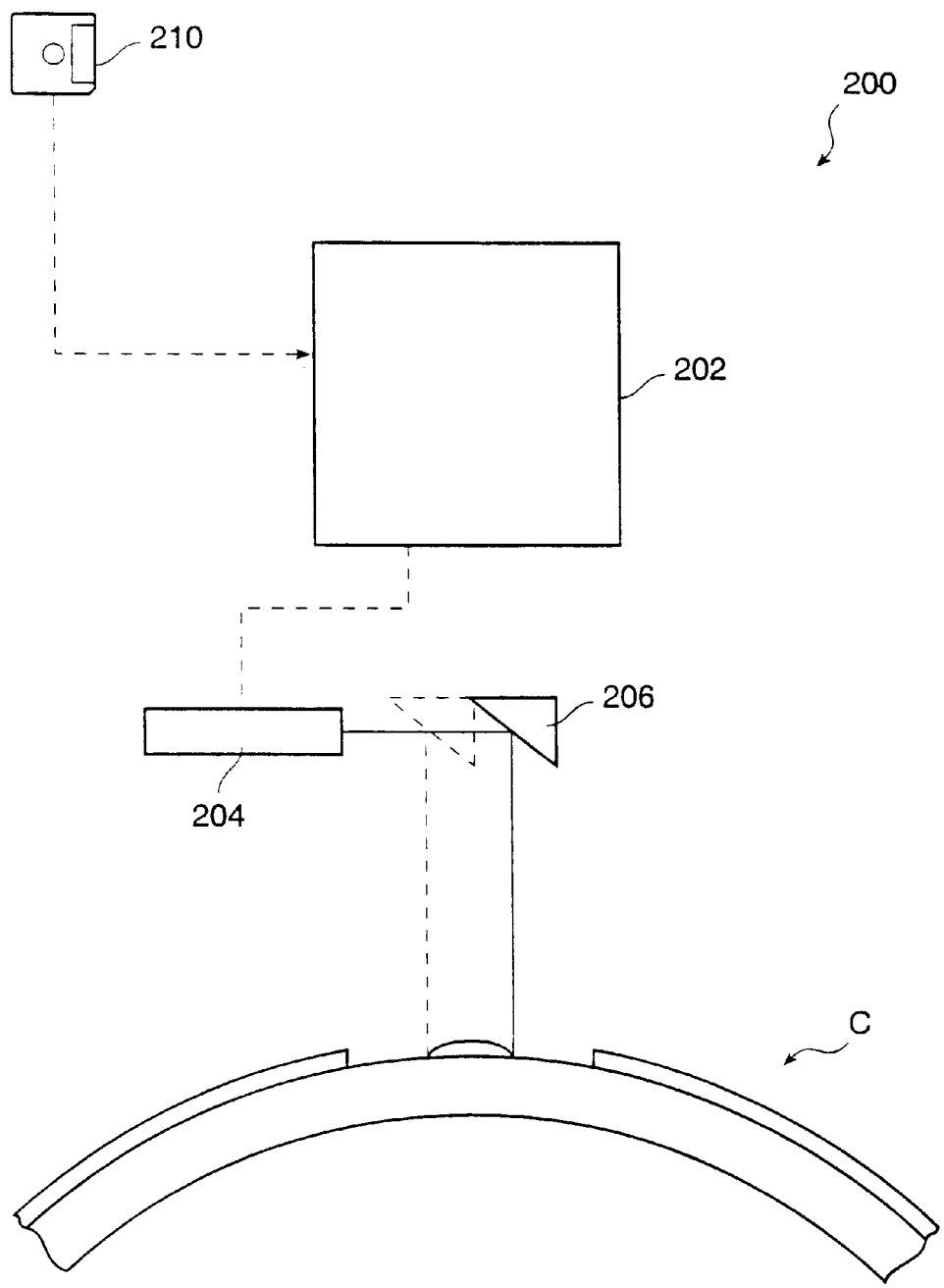
FIG. 4A illustrates an alternative system constructed in accordance with the principles of the present invention.

Referring now to FIG. 4A, an alternative system 200 comprises a controller 202, a laser 204, and a scanning mirror 206 which is positionable via the controller 202. The laser 204 produces a small diameter beam, typically having a diameter in the range from 0.6 mm to 2.0 mm, usually from 0.8 mm to 2.0 mm, and the beam may be scanned over a cornea C using the positionable mirror 206. Thus, the total exposure of the laser radiation against any point on the cornea can be controlled by positioning or varying the angle of mirror 206.

A computer program 210 in the form of a computer-readable disk or other conventional medium is provided as part of the system 200. The computer program 210 encodes methods for scanning the laser beam over the epithelial layer so that peripheral portions of the region of the epithelial layer to be removed can be exposed to a lesser total exposure than the more central regions. As illustrated in FIG. 4A, as the more peripheral regions are removed, the beam can be scanned only over regions of the epithelium which remain.

Figure 8:
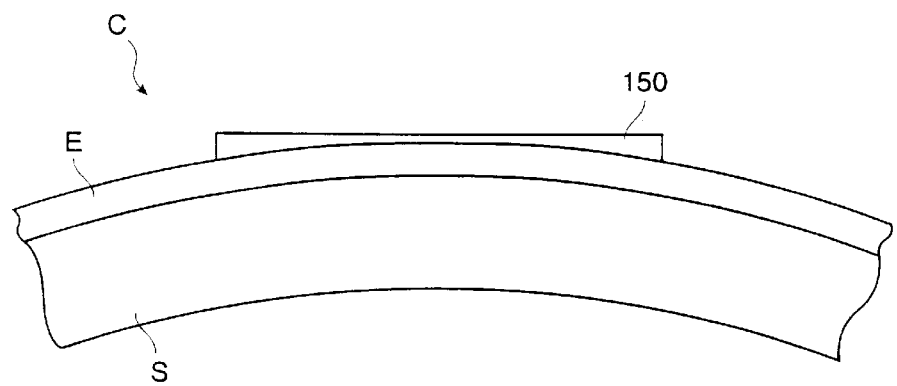
FIGS. 8–10 illustrate use of an ablation mask for performing methods of epithelial layer removal according to the present invention.
Figure 9:
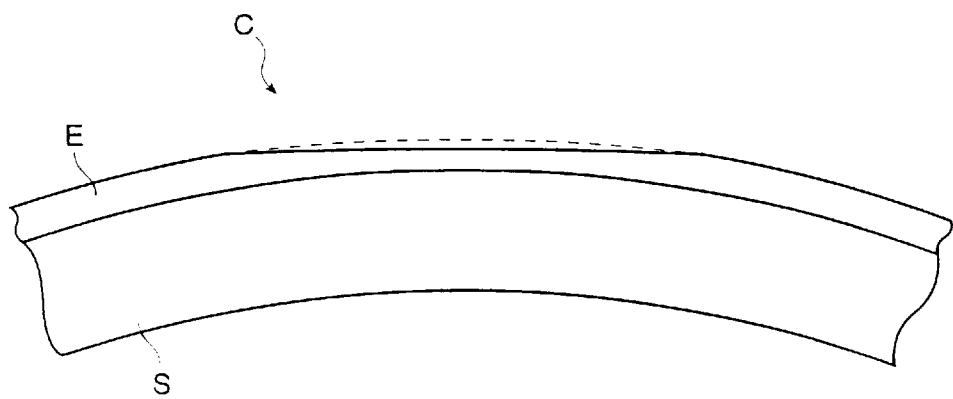
Figure 10:
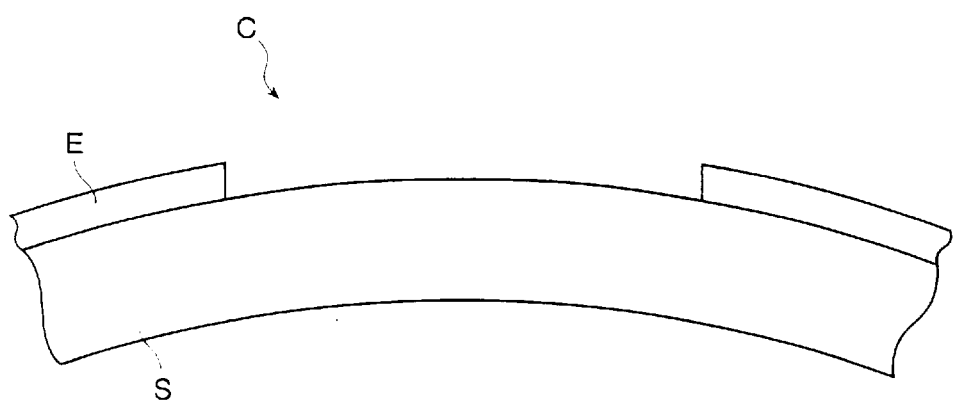

As an alternative to patterning of the ablative beam using an adjustable aperture, the beam may be patterned using an ablation mask 150, as illustrated in FIGS. 8–10. The ablation mask 150 has a profile selected to reduce ablation at the periphery of the region being removed relative to the central region. As shown in FIG. 8, the mask will thus generally be thicker or otherwise treated to resist ablation for a longer time at its periphery than at the central region. The preparation and use of ablation masks is described in detail in U.S. Pat. No. 5,279,611, the full disclosure of which is incorporated herein by reference. After ablation through the mask is completed, the anterior surface of the epithelial layer E will appear as illustrated in FIG. 9, which should be generally as illustrated in connection with FIG. 6. Full ablation using the open aperture can then be continued until the remaining portions of the epithelial layer are removed, as illustrated in FIG. 10. While generally effective, methods of the present invention employing an ablation mask will be less preferred. It will usually be more convenient and more repeatable to use the adjustable aperture to effect modification of the epithelial layer removal rates according to the methods of the present invention.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for removing an epithelial layer from over a stromal layer in a cornea, said method comprising:

irradiating a region of the epithelial layer with ablative radiation for a total exposure, wherein the region has a central portion and an outer peripheral portion; and patterning the ablative radiation in accordance with a pre-programmed sequence so as to cause total exposure to increase from an outer periphery of the outer peripheral portion toward the central portion of the region so as to correct excess ablation of the peripheral portion which would occur in the absence of said patterning.

2. A method as in claim 1, wherein the irradiating step comprises directing a single beam at the epithelial layer.

3. A method as in claim 2, wherein the single beam ablative radiation has a diameter in the range from 0.6 mm to 7.0 mm and a substantially uniform intensity across its width.

4. A method as in claim 3, wherein the single beam ablative radiation has an intensity in the range from 110 to 220 mJ/cm$^2$.

5. A method as in claim 4, wherein the single beam is pulsed.

6. A method as in claim 2, wherein the patterning step comprises:

disposing a diametrically adjustable aperture between a laser radiation source and the cornea; and adjusting the diameter of the aperture in accordance with the pre-programmed sequence so that the aperture is open to expose the entire region of the epithelial layer during a portion of the total exposure period and the aperture adjusts between the open position and a closed position during another part of the exposure period, so as to cause total exposure to increase from the outer periphery of the outer peripheral portion toward the central portion.

7. A method as in claim 1, wherein the irradiating step comprises scanning a small diameter beam over the region of the epithelial layer.

8. A method as in claim 7, wherein the patterning step comprises selectively directing the small diameter beam over the outer peripheral portion of the region for a total exposure less than the total exposure of more central portions, in accordance with the pre-programmed sequence, so as to cause total exposure to increase from the outer periphery of the outer peripheral portion toward the central portion.

* * * * *